United States Patent
Otsuka

(10) Patent No.: US 7,102,028 B2
(45) Date of Patent: Sep. 5, 2006

(54) METHOD FOR PRODUCING 3,5-DI-TERT-BUTYL-4-HYDROXYBENZOIC ACID

(75) Inventor: Ryoichi Otsuka, Nishinomiya (JP)

(73) Assignee: Kabushiki Kaisha Ueno Seiyaku Oyo Kenkyujo, Osaka-fu (JP)

( * ) Notice: Subject to any disclaimer, the term of this patent is extended or adjusted under 35 U.S.C. 154(b) by 0 days.

(21) Appl. No.: 11/139,636

(22) Filed: May 31, 2005

(65) Prior Publication Data

US 2005/0267311 A1 Dec. 1, 2005

(30) Foreign Application Priority Data

May 28, 2004 (JP) ............................. 2004-158968

(51) Int. Cl.
*C07C 51/15* (2006.01)

(52) U.S. Cl. ..................................... 562/424

(58) Field of Classification Search ..................... None
See application file for complete search history.

(56) References Cited

FOREIGN PATENT DOCUMENTS

| EP | 0834494 A1 | 4/1998 |
| GB | 1219205 A | 1/1971 |
| JP | WO 2004/031113 A1 * | 4/2004 |
| JP | WO 2004/078693 A1 * | 9/2004 |
| WO | WO 2004/031113 A1 | 4/2004 |
| WO | WO 2004/078693 A1 | 9/2004 |

OTHER PUBLICATIONS

CAS Abstract of Ueno, Ryuzo et al: "Process for production of hydroxybenzoic acids", STN Database accession No. 2004:756668 for WO 2004/078693 A1 (Kabushiki Kaisha Ueno Seiyaku Oyo Kenkyujo) Sep. 16, 2004.
CAS Abstract of Ueno, Ryuzo et al: "Process for preparation of hydroxybenzoic acids", STN Database accession No. 2004:308393 for WO 2004/031113 A1 (Kabushiki Kaisha Ueno Seiyaku Oyo Kenkyujo) Apr. 15, 2004.

* cited by examiner

*Primary Examiner*—Paul A. Zucker
(74) *Attorney, Agent, or Firm*—Sughrue Mion, PLLC

(57) ABSTRACT

The present invention provides a method for producing 3,5-di-tert-butyl-4-hydroxybenzoic acid comprising:
(1) providing 2,6-di-tert-butylphenol which may contain up to 0.5% by weight of 3,3',5,5'-tetra-tert-butyl-4,4'-dihydroxybiphenyl;
(2) reacting a basic alkali metal compound with an excess amount of the 2,6-di-tert-butylphenol, which is in excess of the basic alkali metal compound, to give the alkali metal 2,6-di-tert-butylphenolate; and
(3) reacting the alkali metal 2,6-di-tert-butylphenolate obtained in step (2) with carbon dioxide to give 3,5-di-tert-butyl-4-hydroxybenzoic acid. According to the method of the present invention, 3,5-di-tert-butyl-4-hydroxybenzoic acid can be obtained with high and stable yield.

13 Claims, No Drawings

METHOD FOR PRODUCING 3,5-DI-TERT-BUTYL-4-HYDROXYBENZOIC ACID

FIELD OF THE INVENTION

The present invention relates to a method for producing 3,5-di-tert-butyl-4-hydroxybenzoic acid.

BACKGROUND OF THE INVENTION 3,5-Di-tert-butyl-4-hydroxybenzoic acid (hereinafter, called as "DBPOB") is used for synthesizing a wide variety of materials, for example ultraviolet absorber and antioxidant contained in polymer materials such as polypropylene, developer for pressure-sensitive recording paper as well as medical and agricultural chemicals.

WO 2004/031113 (which is incorporated herein by reference) discloses a method for producing DBPOB, which comprises reacting a basic alkali metal compound such as sodium hydroxide with an excess amount of 2,6-di-tert-butylphenol (hereinafter, called as "DTBP") at a temperature of no lower than 160° C. to give the alkali metal 2,6-di-tert-butylphenolate and reacting said alkali metal 2,6-di-tert-butylphenolate with carbon dioxide to give DBPOB.

This method is advantageous because of the high reaction yield. In addition, the excess DTBP can easily be recovered from the product and reused for synthesizing DBPOB as starting material.

However, the present inventors have found that when the method was conducted with DTBP which was stored for a long time, the expected high yield could not be achieved though the stored DTBP kept the high purity. Moreover, when the method is conducted repeatedly using the excess DTBP separated at the last step as starting material for the next cycle, the yield of DBPOB decreases after 4 th or 5 th cycles. In this case, though there is no problem concerning the purity of the DTBP separated in the last step of each cycle, the yield of DBPOB decreased dependent on the number of the cycles.

Accordingly, there is a need for a method of producing DBPOB with high and stable yield even if DTBP used for the reaction is the one that has been stored for a long time or excess DTBP is recycled more than 4 or 5 times.

SUMMARY OF THE INVENTION

An object of the present invention is providing a method for preparing 3,5-di-tert-butyl-4-hydroxybenzoic acid with high and stable yield.

The present inventors have revealed here that DTBP is oxidized to give 3,3',5,5'-tetra-tert-butyl-4,4'-dihydroxybiphenyl (hereinafter, called as "TTBBP") during storage or multiple recycling, and that thus generated TTBBPremarkably inhibits the reaction of alkali metal 2,6-di-tert-butylphenolate with carbon dioxide, even in low amount. Accordingly, in the production of DBPOB, DTBP comprising no or sufficiently low amount of TTBBP should be used as starting material.

The first embodiment of the present invention provides a method for producing 3,5-di-tert-butyl-4-hydroxybenzoic acid comprising:
(1) providing 2,6-di-tert-butylphenol which may contain up to 0.5% by weight of 3,3',5,5'-tetra-tert-butyl-4,4'-dihydroxybiphenyl;
(2) reacting a basic alkali metal compound with an excess amount of the 2,6-di-tert-butylphenol, which is in excess of the basic alkali metal compound, to give alkali metal 2,6-di-tert-butylphenolate; and
(3) reacting the alkali metal 2,6-di-tert-butylphenolate obtained in step (2) with carbon dioxide to give 3,5-di-tert-butyl-4-hydroxybenzoic acid.

The second embodiment of the present invention provides a method for producing 3,5-di-tert-butyl-4-hydroxybenzoic acid comprising:
(a) reacting a basic alkali metal compound with an excess amount of 2,6-di-tert-butylphenol, which is in excess of the basic alkali metal compound, to give the alkali metal 2,6-di-tert-butylphenolate;
(b) reacting the alkali metal 2,6-di-tert-butylphenolate obtained in step (a) with carbon dioxide to give 3,5-di-tert-butyl-4-hydroxybenzoic acid;
(c) collecting unreacted 2,6-di-tert-butylphenol from the reaction system after step (b);
(d) purifying 2,6-di-tert-butylphenol collected in step (c) so that the 3,3',5,5'-tetra-tert-butyl-4,4'-dihydroxybiphenyl content in 2,6-di-tert-butylphenol is no more than 0.5% by weight; and
(e) conducting steps (a)–(d) repeatedly using the 2,6-di-tert-butylphenol purified in step (d) for step (a) of the next cycle.

According to the method of the present invention, due to the excess amount of DTBP over the basic alkali metal compound in the reaction, the reaction to give the alkali metal 2,6-di-tert-butylphenolate is promoted. In this method, the excess DTBP also acts as reaction medium and consequently, the high efficient reaction of alkali metal 2,6-di-tert-butylphenolate with carbon dioxide can be attained.

TTBBP content in DTBP used as starting material of step (2) of the first embodiment and step (a) of the second embodiment of the present invention is up to 0.5% by weight, preferably up to 0.3% by weight and most preferably up to 0.1% by weight.

When the TTBBP content is more than 0.5% by weight, the yield of DBPOB will be decreased.

In step (1) of the first embodiment, the amount of TTBBP contained in DTBP may be determined before the reaction. When the amount of TTBBP is no more than 0.5% by weight, DTBP can be used without further purification. When the TTBBP content is more than 0.5% by weight, the DTBP may be purified so that the TTBBP content is up to 0.5% by weight.

Examples of basic alkali metal compounds used for the present invention are alkali metal hydroxide such as sodium hydroxide, potassium hydroxide, C1–4 alkali metal alkoxide such as sodium methoxide, potassium methoxide and alkali metal hydride such as sodium hydride.

Among the above, alkali metal hydroxide and/or C1–4 alkali metal alkoxide are preferable because they are easy to handle. The alkali metal hydroxide and/or C1–4 alkali metal alkoxide may be provided as solution in water or a C1–4 alcohol. In step (2) of the first embodiment and step (a) of the second embodiment of the present invention, water or C1–4 alcohol is produced as byproduct when an alkali metal hydroxide or C1–4 alkali metal alkoxide is employed.

Water and/or C1–4 alcohol inhibits the reaction of step (3) of the first embodiment and step (b) of the second embodiment and therefore, should be removed so that the reaction system of step (3) or (b) contains substantially no water and/or C1–4 alcohol.

The method of removing water and/or C1–4 alcohol is not limited, and it is preferable to remove the byproduct during step (2) of the first embodiment and step (a) of the second embodiment under atmospheric pressure. Preferably, water and/or C1–4 alcohol is removed by feeding an inert gas, such as nitrogen, helium or argon gas, into the reaction container so that water/alcohol is distilled off. In addition, the pressure of the reaction system under inert gas flow may be reduced to the level where DTBP is not vigorously distilled.

The removal of water and/or C1–4 alcohol may be conducted at 80–300° C., more preferably at 120–200° C. If the temperature is lower than 80° C., the reaction rate to give alkali metal 2,6-di-tert-butylphenolate will be decreased. On the contrary, if the temperature is higher than 300° C., DTBP might be distilled out of the reaction and DTBP and alkali metal 2,6-di-tert-butylphenolate might be thermally decomposed.

In general, C1–4 alcohol is easier to be removed than water from a system in which an alkali metal salt of aromatic hydroxy compound is present. Accordingly, C1–4 alkali metal alkoxide alone is preferably used as basic alkali metal compound in the present method. Among C1–4 alkali metal alkoxides, sodium methoxide is especially preferable because it is available at low cost and it generates methanol, which can easily be removed from the reaction system, upon the reaction with DTBP.

In the present specification and claims, "excess" amount of DTBP means that the amount of the DTBP is two or more molar parts per 1 molar part of the basic alkali metal compound. In the present invention, the amount of the DTBP used in step (2) of the first embodiment and step (a) of the second embodiment is preferably 2–30 molar parts, more preferably 3–20 molar parts and even more preferably 4–15 molar parts per 1 molar part of the basic alkali metal compound. In case where the amount of DTBP is less than 2 molar parts, the yield of DBPOB will be decreased because of interfering with homogeneous stirring due to high viscosity of the reaction. Using more than 30 molar parts of DTBP is permissible, but it will not cause in better result than using less amount of DTBP and therefore, it is not economical.

In step (2) of the first embodiment and step (a) of the second embodiment, liquid DTBP itself may act as solvent and therefore, it is not necessary to add another solvent to the reaction system. However, a solvent other than DTBP may be added to the reaction and the embodiment is also included in the scope of the present invention.

Examples of solvents which may be used in step (2) of the first embodiment and step (a) of the second embodiment and/or step (3) of the first embodiment and step (b) of the second embodiment are light oil, kerosene, gasoline, white oil, alkylbenzene, alkylnaphthalene, diphenyl, diphenylalkane, alkyldiphenyl, triphenyl, triphenyl hydride, diphenylether, alkylphenylether, alkyldiphenylether, higher alcohol such as iso-octyl alcohol and a mixture thereof.

In step (3) of the first embodiment and step (b) of the second embodiment, the reaction of alkali metal 2,6-di-tert-butylphenolate with carbon dioxide may be conducted in any manner known to the art and may be by means of batch-wise reaction or continuous reaction.

The reaction of the alkali metal 2,6-di-tert-butylphenolate with carbon dioxide may be carried out in an autoclave under the carbon dioxide pressure of preferably from atmospheric pressure to 5 MPa (G), more preferably 0.2–1 MPa (G) at a reaction temperature of preferably 160–300° C., and more preferably 170–290° C.

The reaction time may vary depending on the carbon dioxide pressure and the reaction temperature, and in general, it may be 0.5–6 hrs, and preferably 1–4 hrs.

After the reaction was completed, water is added to the reaction mixture comprising the alkali metal salt of DBPOB, and then the mixture is separated into the organic and aqueous phases. The aqueous phase, i.e. an aqueous solution of the alkali metal salt of DBPOB, is added with an acid to precipitate DBPOB. The precipitates may be collected by filtration or centrifugation to give crystalline DBPOB.

The organic phase consists of DTBP or DTBP and the other solvent added to the reaction. When the content of TTBBP in the organic phase is no more than 0.5% by weight, the organic phase separated from the reaction mixture may be used again for synthesizing DBPOB as starting material as it is. If it is desired, the organic phase may be purified before use by means of, such as, filtration or carbon treatment so that impurities such as colorant and insoluble matters are removed.

When the content of TTBBP in the organic phase is more than 0.5% by weight, the organic phase must be purified before being used again as starting material for synthesizing DBPOB. Purification of DTBP containing more than 0.5% by weight of TTBBP may be conducted by any means as long as the contaminated TTBBP can be effectively removed. For example, distillation and chromatographic separation may be employed. Among them, distillation is preferable because it can be conducted with simple instrument and procedures.

According to the present invention, distillation is preferably carried out under reduced pressure at 80–200° C. The distillation pressure may vary dependent on the temperature, and typically, is 1–100 Torr.

The distillation can be conducted under atmospheric pressure at a temperature higher than the boiling point of DTBP (about 253° C.), but such a high temperature is not preferable since DTBP might be decomposed. Actually, DTBP tend to be decomposed at a temperature higher than 200° C. and therefore, the temperature is preferably kept below 200° C. even if the distillation step is carried out under reduced pressure.

According to the method of the present invention, 3,5-di-tert-butyl-4-hydroxybenzoic acid can be produced with high and stable yield.

3,5-di-tert-butyl-4-hydroxybenzoic acid produced by the method of the present invention is highly pure and can be used for manufacturing materials, for example, ultraviolet absorber and antioxidant contained in polymer materials such as polypropylene, developer for pressure-sensitive recording paper as well as medical and agricultural chemicals.

The present invention is further described in reference to the following examples. The examples are intended to illustrate the invention and are not to be construed to limit the scope of the invention.

EXAMPLES

Referential Example 1800 g of DTBP comprising 0.62% by weight of TTBBP was heated to 120° C. under reduced pressure, 50 Torr, with stirring. DTBP was distilled at this temperature and the temperature was kept until 1400 g of DTBP was distilled. Thus purified DTBP contained 0.01% by weight of TTBBP.

Example 1

1207 g (5.85 moles) of DTBP comprising 0.01% by weight of TTBBP, which was obtained in referential example, and 86.8 g (0.45 moles) of 28% solution of sodium methoxide in methanol were fed in an 2 L stainless-steel vessel equipped with a magnetic stirrer, a thermometer, pressure gauge and alcohol-separator.

The reaction mixture was heated to 180° C. under nitrogen gas flow and reacted at the temperature for 2 hrs. At the same time, methanol was distilled off. Thus obtained slurry of sodium salt of DTBP was heated to 200° C. The nitrogen gas in the vessel was replaced with carbon dioxide gas and carboxylation reaction was carried out under the $CO_2$ pressure of 6 kgf/cm$^2$ (G) with stirring for 2 hrs. After the reaction was completed, the reaction mixture was cooled to 90° C. and 1200 g of water was added thereto. The obtained mixture was separated into the aqueous and organic phases at 85° C.

To thus obtained aqueous phase, 73% aqueous sulfuric acid was added and the pH was adjusted to 3.8 to precipitate 3,5-di-tert-butyl-4-hydroxybenzoic acid. The precipitated crystal was filtrated, washed with water and dried. As a result, 101.6 g of 3,5-di-tert-butyl-4-hydroxybenzoic acid was obtained. The yield to the fed amount of sodium methoxide was 90.2%.

COMPARATIVE EXAMPLE 1

3,5-di-tert-butyl-4-hydroxybenzoic acid was prepared in the same manner as Example 1 except that DTBP containing 0.62% by weight of TTBBP was used. 85.4 g of 3,5-di-tert-butyl-4-hydroxybenzoic acid was obtained. The yield to the fed amount of sodium methoxide was 75.8%.

COMPARATIVE EXAMPLE 2

The same method as Example 1 was carried out repeatedly except that the organic phase obtained in the last step was used for the starting material of the next cycle. To the organic phase obtained in the every last step, DTBP containing 0.01% by weight of TTBBP was added to adjust total weight of the starting DTBP for the next cycle to 1207 g. After five cycles were conducted, the organic phase, i.e. DTBP, contained 1.58% by weight of TTBBP.

The 6 th cycle was carried out in the same manner as Example 1 except that the DTBP obtained in the last step of the 5 th cycle, which contained 1.58% by weight of TTBBP, was used for the starting material. After the carboxylation reaction was completed, water was added to the mixture and then, the mixture was separated into the aqueous and organic phases. Thus obtained organic phase was 1150 g and contained 1.68% by weight of TTBBP.

To the water phase, 73% aqueous sulfuric acid was added and the pH was adjusted to 3.8 to precipitate 3,5-di-tert-butyl-4-hydroxybenzoic acid. The precipitated crystal was filtrated, washed with water and dried. As a result, 64.2 g of 3,5-di-tert-butyl-4-hydroxybenzoic acid was obtained. The yield of the 6 th cycle to the fed amount of sodium methoxide was 57%.

Example 2

The organic phase obtained in the 6th cycle in Comparative Example 2, i.e. 1150 g of DTBP containing 1.68% by weight of TTBBP was used. The organic phase was purified in the same manner as described in Referential Example and 920 g of DTBP containing 0.03% of TTBBP was obtained. Thus purified organic phase was added with 287 g of DTBP containing 0.01% by weight of TTBBP to give 1207 g of DTBP containing 0.03% by weight of TTBBP. 3,5-di-tert-buthyl-4-hydroxy benzoic acid was prepared in the same manner as Example 1 using thus obtained DTBP for the starting DTBP. After the carboxylation reaction was completed, water was added to the mixture and then, the mixture was separated into the water and organic phases.

To the water phase, 73% aqueous sulfuric acid was added and the pH was adjusted to 3.8 to precipitate 3,5-di-tert-butyl-4-hydroxybenzoic acid. The precipitated crystal was filtrated, washed with water and dried. As a result, 105 g of 3,5-di-tert-butyl-4-hydroxybenzoic acid was obtained. The yield to the fed amount of sodium methoxide was 93.2%.

What is claimed is:

1. A method for producing 3,5-di-tert-butyl-4-hydroxybenzoic acid comprising:
   (1) providing 2,6-di-tert-butylphenol which may contain up to 0.5% by weight of 3,3',5,5'-tetra-tert-butyl-4,4'-dihydroxybiphenyl;
   (2) reacting sodium methoxide with an excess amount of the 2,6-di-tert-butylphenol, which is excess of sodium methoxide, to give sodium 2,6-di-tert-butylphenolate; and
   (3) reacting the sodium 2,6-di-tert-butylphenolate obtained in step (2) with carbon dioxide to give 3,5-di-tert-butyl-4-hydroxybenzoic acid.

2. The method according to claim 1, wherein step (1) comprises purifying 2,6-di-tert-butylphenol so that the 3,3',5,5'-tetra-tert-butyl-4,4'-dihydroxybiphenyl content in 2,6-di-tert-butylphenol is no more than 0.5% by weight.

3. The method according to claim 1, wherein the 3,3',5,5'-tetra-tert-butyl-4,4'-dihydroxybiphenyl content in 2,6-di-tert-butylphenol is no more than 0.3% by weight.

4. The method according to claim 2, wherein 2,6-di-tert-butylphenol is purified so that the 3,3',5,5'-tetra-tert-butyl-4,4'-dihydroxybiphenyl content in 2,6-di-tert-butylphenol is no more than 0.3% by weight.

5. The method according to claim 1, wherein in step (2) sodium methoxide and 2,6-di-tert-butylphenol are reacted at a temperature of 80–300° C. and at the same time alcohol, which is generated as byproduct, is distilled away from the reaction.

6. The method according to claim 1, wherein the starting amount of 2,6-di-tert-butylphenol is 2–30 fold moles to sodium methoxide.

7. The method according to claim 2, wherein 2,6-di-tert-butylphenol is subjected to distillation under reduced pressure at a temperature of 80–200° C.

8. A method for producing 3,5-di-tert-butyl-4-hydroxybenzoic acid comprising:
   (a) reacting sodium methoxide with an excess amount of 2,6-di-tert-butylphenol, which is in excess of sodium methoxide, to give sodium 2,6-di-tert-butylphenolate;
   (b) reacting the sodium 2,6-di-tert-butylphenolate obtained in step (a) with carbon dioxide to give 3,5-di-tert-butyl-4-hydroxybenzoic acid;
   (c) collecting unreacted 2,6-di-tert-butylphenol from the reaction system after step (b);
   (d) purifying 2,6-di-tert-butylphenol collected in step (c) so that the 3,3',5,5'-tetra-tert-butyl-4,4'-dihydroxybiphenyl content in 2,6-di-tert-butylphenol is no more than 0.5% by weight; and
   (e) conducting steps (a)–(d) repeatedly using the 2,6-di-tert-butylphenol purified in step (d) for step (a) of the next cycle.

9. The method according to claim 8, wherein in step (d) 2,6-di-tert-butylphenol is purified so that the 3,3',5,5'-tetra-tert-butyl-4,4'-dihydroxybiphenyl content in 2,6-di-tert-butylphenol is no more than 0.3% by weight.

10. The method according to claim 8, wherein in step (a) sodium methoxide and 2,6-di-tert-butylphenol are reacted at a temperature of 80–300° C. and at the same time alcohol, which is generated as byproduct, is distilled away from the reaction.

11. The method according to claim 8, wherein the starting amount of 2,6-di-tert-butylphenol is 2–30 fold moles to sodium methoxide.

12. The method according to claim 8, wherein in step (d) 2,6-di-tert-butylphenol is subjected to distillation under reduced pressure at a temperature of 80–200° C.

13. The method according to claim 8, wherein the steps (a)–(d) are repeatedly conducted no less than five times.

* * * * *